United States Patent
Bernasconi et al.

(10) Patent No.: US 6,586,190 B2
(45) Date of Patent: Jul. 1, 2003

(54) PARALLEL HIGH THROUGHPUT METHOD AND KIT

(75) Inventors: Paul Bernasconi, Chapel Hill, NC (US); Ray Donald Carpenter, Durham, NC (US); Gary Keith Powell, Morrisville, NC (US); Robert Michael Petrovich, Cary, NC (US); Kimberly Ann White, Durham, NC (US); Jennifer Audrey Hunt, Raleigh, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/918,109

(22) Filed: Jul. 30, 2001

(65) Prior Publication Data

US 2002/0137888 A1 Sep. 26, 2002

Related U.S. Application Data

(60) Provisional application No. 60/226,141, filed on Aug. 18, 2000.

(51) Int. Cl.[7] .................. G01N 33/53; C12N 11/00; C12N 5/06; C12N 1/00
(52) U.S. Cl. .................. 435/7.1; 435/7.2; 435/174; 435/334; 435/810
(58) Field of Search .................. 435/7.1, 7.2, 174, 435/334, 810

(56) References Cited

U.S. PATENT DOCUMENTS

| | | | |
|---|---|---|---|
| 5,223,409 A | 6/1993 | Ladner et al. | 435/69 |
| 5,571,698 A | 11/1996 | Ladner et al. | 435/69.7 |
| 5,736,330 A | 4/1998 | Fulton | 435/6 |
| 5,981,180 A | 11/1999 | Chandler et al. | 435/6 |
| 6,057,107 A | 5/2000 | Fulton | 435/6 |

FOREIGN PATENT DOCUMENTS

| | | | | |
|---|---|---|---|---|
| WO | WO 98/19162 | 5/1998 | | |
| WO | WO 99/06839 | 2/1999 | | |
| WO | WO 99 19515 | 4/1999 | ............ | C12Q/1/68 |
| WO | WO 95/54728 | 10/1999 | | |
| WO | WO 00/52153 | 9/2000 | | |
| WO | WO 01 77391 A | 10/2001 | ............ | C12Q/1/68 |
| WO | WO 02/04956 A2 | 1/2002 | | |

OTHER PUBLICATIONS

Crameri et al, *Selective Enrichment and High–Throughput Screening of Phage Surface–Displayed CDNA Libraries from Complex Allergenic Systems Combinatorial Chemistry and High Throughput Screening*, vol. 2, No. 2 (Apr. 1999), pp. 63–72.

Hyde–Deruyscher R. et al, *Detection of Small–Molecule Enzyme Inhibitors with Peptides Isolated from Phage–displayed Combinatorial Peptide Libraries* Chemistry & Biology (London), vol. 7, No. 1 (Jan. 2000) pp. 17–25.

(List continued on next page.)

*Primary Examiner*—Hankyel T. Park
(74) *Attorney, Agent, or Firm*—Bruce Vrana (57) ABSTRACT

A parallel high throughput method and kit for the discovery of small molecule interactors of target proteins, in particular, target proteins expressed from entire genomes or subsets thereof. The target module is prepared by binding selectively a target protein, modified to allow its detection, to a surrogate ligand that is linked to an individually detectable bead. Sets of target modules are mixed together in each chamber of a multi-chamber container. A test compound or collection of test compounds is added to each chamber, and the interaction of a compound with each target module is observed. A compound that is specific for a particular target protein will displace that protein from its target module. The identity of the target module so disrupted is determined by identifying the particular bead to which the displaced target protein was attached.

27 Claims, 2 Drawing Sheets

OTHER PUBLICATIONS

Barrett, R.W. et al., *Selective Enrichment and Characterization of High Affinity Ligands from Collections of Random Peptides on Filamentous Phage Analytical Biochemistry,* vol. 204 (1993) pp. 357–364.

Cwirla, et al. *Peptides on phage: A vast library of peptides for identifying ligands Proceedings of the National Academy of Sciences,* vol. 87 (Aug. 1990) pp. 6378–6382.

High Throughput Screening: 1999/2000 Market Analysis for Life Science Manufacturers, 1999 Clinical Marketing Consultants.

Iannone, Marie A., et al. *Multiplexed Molecular Interactions of Nuclear Receptors Using Fluorescent Micropheres Cytometry,* vol. 44 (2001) pp. 326–336.

Ladner, R. and Ley, A.A., *Novel Frameworks as a Source of High–Affinity Ligands Current Opinion in Biotechnology,* vol. 12, no. 4 (Aug., 1, 2000) pp. 406–410.

Scott, J.K. and Smith, G.P. *Searching for Peptide Ligands with an Epitope Library Science,* vol. 249 (1990) pp. 386–390.

Smith, G.P. *Filamentous fusion phage: novel expression vectors that display cloned antigens on the viron surface. Science,* vol. 228 (1985) pp. 1315–1317.

Lam et al., *A New Type of Synthetic Peptide Library for Identifying Ligand–Binding Activity Nature,* vol. 354 (Nov. 7, 1991), pp. 82–84.

Marks et al., *By–passing Immunization; Human Antibodies from V–gene Libraries Displayed on Phage Journal of Molecular Biology,* vol. 222 (1991), pp. 581–597.

PARALLEL HIGH THROUGHPUT METHOD AND KIT

CROSS REFERENCE TO RELATED APPLICATIONS

This application claims the benefit of U.S. Provisional Application No. 60/226,141, filed Aug. 18, 2000.

FIELD OF THE INVENTION

The present invention is directed to a high throughput method and kit for the discovery of small molecule interactors of target proteins, in particular to a high throughput method and kit for parallel analysis of small molecule interactions with a multitude of target proteins of unknown function.

BACKGROUND OF THE INVENTION

Single target High Throughput Screens (HTS) are the method of choice to discover small molecule inhibitors, ligands, agonists or antagonists of specific target proteins in both the Agricultural and Pharmaceutical Research communities. These screens are performed on robotic platforms that can test 100,000 to over a million compounds against one target protein. Several detection methods, ranging from radiolabeled tracers to elaborate fluorescence markers, are currently used. For each target protein to be screened, investigators must know its particular enzymatic or regulatory function in order to identify and prepare a proper substrate or ligand, and to develop a proper workable detection method. Gene products that are known to have a useful physiological role, but whose enzymatic or regulatory function is unknown, are not used as targets in HTS. Thus, this approach requires a large investment in assay development and implementation, allowing only a limited number of target protein HTS to be performed in a given time period.

Whole genome sequencing projects are forcing a shift in the traditional approach to the HTS research paradigm. One important outcome of these sequencing efforts is the identification of large collections of validated targets. However, because the current approaches to small molecule discovery are based on the single target HTS model, scientists are unable to efficiently use and exploit the vast amount of genomics information being generated. Thus, only highly validated targets warrant the development of unique screens, i.e. targets of known function. In addition, the function of a large portion of the newly discovered validated targets is unknown, making the development of a single target HTS impossible in these cases. Clearly, current single target HTS approaches have severe economic, feasibility, and logistic limitations Thus, a HTS capable of analyzing more than just a few targets without development of unique screens for each target would provide a significant advantage in the field of genomic analysis. In addition, an HTS capable of analyzing a large number of targets of unknown function would also provide a significant advantage in the field of genomic analysis.

SUMMARY

The present invention brings together gene cloning and expression, protein purification and modification, ligand identification and synthesis, and assay platform technologies into a novel screen and method that allows for the parallel, massively multiplexed screening of targets on a genomic scale. The present invention further provides a screen and method capable of analyzing in a HTS manner a multitude of targets of unknown function. A protein of unknown function is any protein for which one cannot associate enzymatic, regulatory, structural or receptor activity.

In the preferred embodiment, the method and kit of the present invention use a collection or plurality of gene products, otherwise referred to herein as "target proteins," based on genomics information about their essentiality to a physiological process. The method and kit of the present invention do not require, however, that the enzymatic or regulatory function of the target proteins be known, nor, for that matter, their essentiality.

In accordance with the present invention, the gene coding for each desired target protein is prepared, transferred into an expression vector and moved into an appropriate host organism, for example *E. coli,* baculovirus, mammalian cells, or yeast. The gene products or target proteins are expressed and then purified.

The purified target proteins are biotinylated and used to pan for phages displaying foreign peptides on their surfaces. Phages containing peptide sequences that bind selectively to the purified target proteins are separately amplified and the DNA encoding the peptides sequenced. The peptide sequences encoded by the DNA are synthesized and used as the surrogate ligands in the method and kit of the present invention.

A target module is prepared by binding selectively a target protein, modified to allow its detection, with a surrogate ligand that is linked to an individually detectable bead. In one embodiment of the present invention, 100 target modules are constructed for 100 target proteins of interest. The 100 target modules are mixed together in each chamber of a multi-chamber container. A compound or collection of compounds to be tested is added to each chamber, and the interaction of a compound with each target module is observed. In the preferred embodiment, analysis of the interaction is implemented by flow cytometry. A compound that is specific for a particular target protein will displace that protein from its target module. The identity of the target module so disrupted is determined by identifying the particular bead to which the surrogate ligand is attached.

In more detail, the method of the present invention includes the steps of obtaining a plurality of target proteins; obtaining a first set of surrogate ligands, wherein each surrogate ligand in the set of surrogate ligands binds selectively to a first target protein; binding the first set of surrogate ligands to first detectable beads to form a first set of surrogate ligand-bead complexes, wherein the first detectable beads can all be detected by the optical characteristics of the first detectable beads; combining the first set of surrogate ligand-bead complexes with the target protein labeled for detection to form a first target module; repeating the above steps, either concurrently or subsequently with a different set of surrogate ligands and detectable beads, and with either the first target protein or a different target protein, to form sets of target modules; adding the sets of target modules to each chamber of a multi-chamber container; adding a test compound, or a collection of test compounds, to each chamber of the multi-chamber container; detecting displacement of a target protein with a test compound; and determining the identity of each target protein that is displaced with a test compound.

The method of the invention further includes obtaining each said set of surrogate ligands by obtaining a phage library, wherein each phage of the library displays foreign peptides; mixing the phage library with each target protein of the plurality of target proteins; isolating phages displaying the foreign peptides that bind selectively to each target protein; isolating DNA encoding the foreign peptides that bind selectively to each target protein; sequencing the DNA; and synthesizing the set of surrogate ligands based on the sequencing.

The method of the invention further includes obtaining the plurality of target proteins by selecting target genes from a genome; expressing each of the target genes to produce the plurality of target proteins; and purifying the target proteins.

The method includes biotinylating the target proteins and linking the target proteins with avidin-phycoerythrin.

The invention further provides target proteins by selecting target genes from a genome, expressing each of the target genes to produce the set of target proteins, and purifying the target proteins.

The invention further provides using a surrogate ligand selected from the group including a peptide, RNA aptamer, and β-peptide. Surrogate ligands may also be selected from small molecules derived from combinatorial chemistry or from natural compound collections.

The invention also provides screening target proteins having unknown function.

The invention further provides labeling each individual bead with a defined combination of two dyes.

The invention further provides labeling each individual bead with a defined combination of three dyes.

The invention further provides labeling each individual bead with a defined population of quantum dots.

The invention also provides screening with 100 beads such that 100 target proteins are screened in each chamber of a multi-chamber container.

The invention also provides screening with 1000 beads such that 1000 target proteins are screened in each chamber of a multi-chamber container.

The invention further provides screening with an amount of test compound per chamber within the range of 0.1 ng to 100 ng.

The invention also provides for a kit that screens a plurality of target proteins derived from a genome the kit comprising sets of target modules, wherein each set of the sets of target modules comprises individually detectable beads; a set of surrogate ligands attached to the detectable beads, wherein the surrogate ligands of the set of surrogate ligands are bound selectively to the same or different target protein of the plurality of target proteins; wherein the target proteins are labeled for detection; and a multi-chamber container, wherein the sets of target modules are stored in each chamber of the multi-chamber container.

The invention also provides for a method for high throughput screening using individually detectable beads, surrogate ligands, and a plurality of target proteins comprising: combining in a chamber a plurality of target modules, each target module comprising a ligand-bead complex and a target protein labeled for detection; wherein the ligand-bead complex comprises a surrogate ligand coupled to an individually detectable bead; wherein each surrogate ligand is selected for use in the method according to a peptide sequence thereof that is known to bind selectively to one of the target proteins; adding to each of the plurality of detection chambers a test compound, whereby the compound displaces the target proteins from the target modules to which target compounds interact, detecting displacement of a target protein with a test compound; and determining the identity of each target protein that is displaced with a test compound.

The invention further provides a method for high throughput screening using individually detectable beads, surrogate ligands, and a plurality of target proteins, the improvement comprising, combining in each chamber of a multi-chamber container sets of target modules, wherein each target module within each set of the sets of target modules comprises a ligand-bead complex and a target protein labeled for detection; wherein the ligand-bead complex comprises a surrogate ligand coupled to an individually detectable bead; wherein each surrogate ligand binds selectively to one of the target proteins; adding to each chamber of the multi-chamber container a test compound, whereby the compound displaces the target proteins from the target modules to which the target compounds interact; detecting displacement of a target protein with a test compound; and determining the identity of each target protein that is displaced with a test compound.

It being understood that the order of the steps of the method of the present invention is not critical and that other orders are possible.

DETAILED DESCRIPTION OF THE INVENTION

Gene Cloning and Expression of Targets

Figure 1:
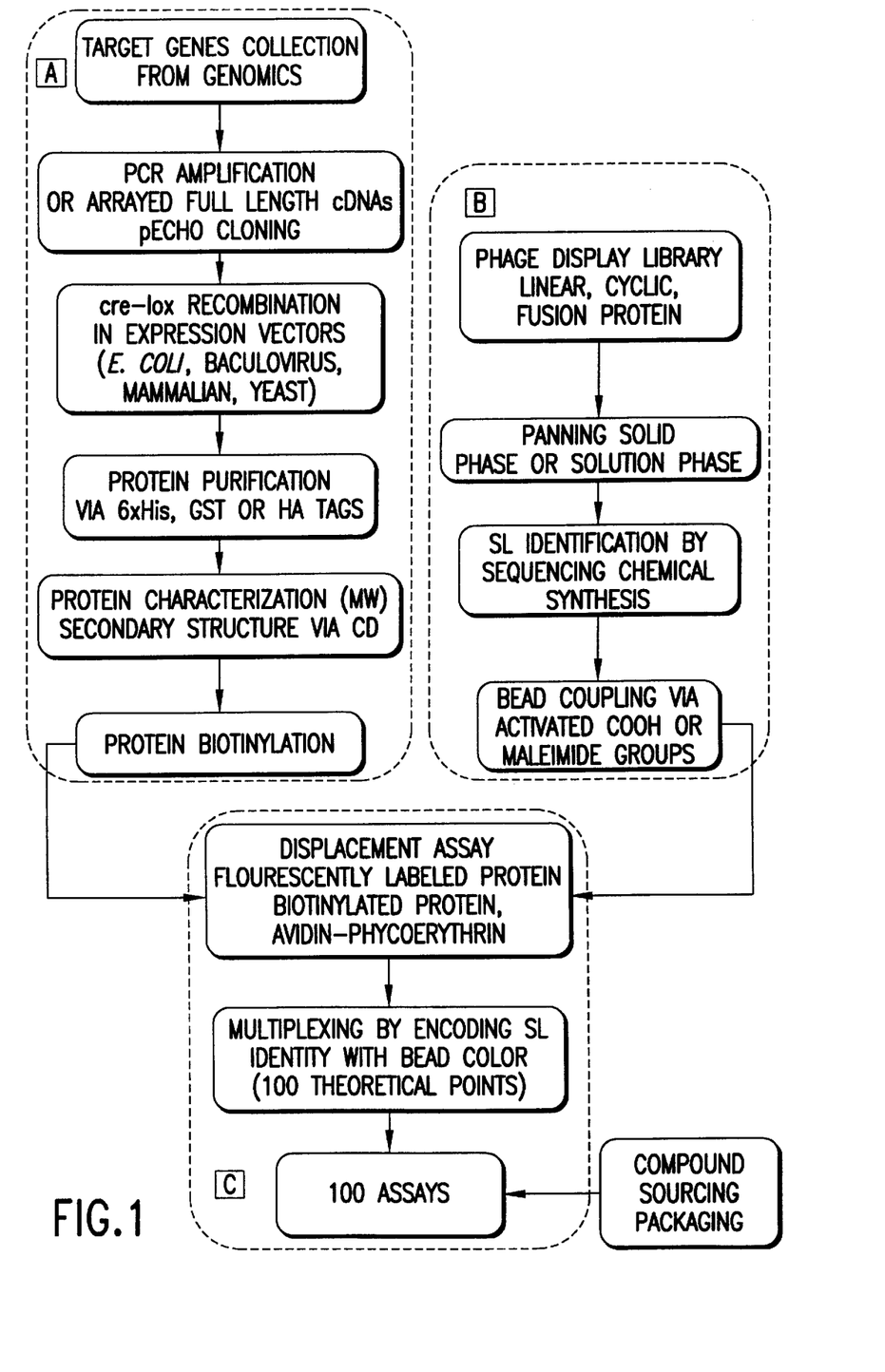
FIG. 1 is a flow diagram of the method of the present invention.

FIG. 1, Section A illustrates the general steps for cloning genes of interest and expression and purification of the corresponding target proteins. Gene products or proteins are considered to be target proteins when they have shown potential as targets for pesticide or drug design work, as determined by knock-out, mis-expression, or gene disruption experiments. In the preferred embodiment of the invention, a collection of genes of interest may consist of the whole genome of a particular organism. A useful collection might consist of 96 genes of interest or multiples thereof, since they can be processed in parallel using microtiter plate based equipment.

A set of two PCR primers for each of these genes is derived from the sequence and used to amplify the corresponding cDNA. The template can be a first strand cDNA obtained by reverse transcription of a population of mRNAs or double stranded cDNA prepared by purifying DNA from a plasmid or phage library. The amplified material is used in a versatile cloning system such as Echo™ Cloning System which uses Cre recombinase for directional cloning from a universal donor vector into a variety of expression vectors (InVitrogen, Carlsbad, Calif.), or GATEWAY Cloning Technology (LifeSciences, GIBCO-BRL, Rockville, Md.) which uses bacteriophage lambda-based site-specific recombination for cloning into a variety of expression vectors. (Current Bio. (1998), 8:1300; Ann. Rev. Biochem. (1989), 58:913; and Ptashe, (1992) A Genetic Switch, Cell Press, Cambridge) The proper orientation is checked by PCR with external and internal primers.

Using the Echo™ Cloning System, genes of interest are transferred into an *E. coli,* baculovirus, mammalian cell or yeast expression vector. For ease of target protein purification, the expression vectors can contain an affinity tag such as GST (glutathione-S-transferase), allowing purification by GSH-agarose chromatography (Smith et al. (1986) PNAS 83:8703–8707), 6xHistidine, allowing protein purification on metal chelate chromatography (Porath et al. (1975) Nature 258:598), or other affinity tags (Ausubel et al., Current Protocols in Molecular Biology, John Wley and Sons (1995)) Alternatively, the expression vector may not provide any tag and the protein is purified either by differential centrifugation (using inclusion bodies), hydrophobic interaction, or ion exchange chromatography. The whole process is run in a parallel fashion in 96-well plates, which are used for the primer preparation, PCR reactions, E. coli transformation and DNA template preparations. A robotic liquid handler such as Tecan Genesis (Tecan AG, Switzerland) or Qiagen Biorobot 9600 (Qiagen GmbH, Germany) is used for the formatting of the PCR reactions. Colony picking is handled by a robot such as Genetix Q-bot (Genetix Ltd, UK).

In one embodiment of the invention, the cloned target protein is expressed in E. coli using conventional inducible promoters such as the tac promoter, arabinose promoter, or T7 promoter (Ausubel et al., Current Protocols in Molecular Biology, John Wiley and sons, 1995). Expression in E. coli is achieved in a wide range of possible genetic backgrounds. The lack of proteases is a well know way of improving expression level (Messing (1983) Methods Enzymol 101:20–78), this system has been recently improved by the suppression of the lonA protease, an ATP dependent enzyme responsible for most of the proteolytic activity in the bacterial cytoplasm. Thomas et al. (1993) Gene 136:237–242 Other genetic characteristics are also useful, such as the ones in the so-called "Origami™" strains which have mutations in both thioredoxin reductase (trxB) and glutathione reductase (gor) genes, which greatly enhances disulfide bond formation in the cytoplasm of E. coli (Aslund et al. (1999) inNovations 10, 11–12). The cloned target can also be expressed in yeast using a galactose inducible promoter (Johnston and Davis (1984) Mol. Cell. Biol. 4:1440–1448), in baculovirus infected insect cells using the polyhedrin promoter (Maiorella et al. (1988) Bio/Technology 6:1406–1410) or in mammalian cells using the CMV promoter (Kaufman (1990) Meth. Enzymol. 185:487–511).

The target protein encoded and expressed by each gene of interest is purified using existing parallel one-step techniques such as the ones offered by Pierce (Rockford, Ill.) and Qiagen. The expected molecular weight of the target proteins are confirmed by SDS-PAGE or by mas spectrometry methods such as MALDI-TOF. Since the method of the present invention is also applicable to proteins of unknown function, some indication that the protein is folded properly is needed. In absence of an activity to measure, the presence of target protein folding is confirmed by CD spectroscopy. For that purpose highly sensitive instruments such as π*-180 (Applied Photophysics, UK) is used. When inclusion bodies are used for purification of the protein, the protein is completely denatured by incubation with 6 M guanidine-HCl and then refolded by dialysis against guanidine-HCl free buffer or by serial dilutions in buffers containing decreasing concentrations of guanidine-HCl. Refolding is followed by CD spectroscopy.

In another embodiment of the present invention, PCR amplification of targets can be substituted by the use of a full-length cDNA library of the organism of interest. As genomics advances, it is expected that these libraries in the universal vectors described above will be available. Such a library is arrayed in a series of 96-well plates, each containing a defined cDNA. For example, the complete complement of the 6000 yeast expressed proteins can be arrayed, according the present invention, in less than 65 96-well plates.

Surrogate Ligand Preparation

A surrogate ligand is a peptide, RNA, beta-peptide or other molecule that has been identified as having an affinity for a given protein. The surrogate ligand acts as a replacement for the physiologically relevant ligand in displacement assays, thereby allowing the design of high throughput displacement assays of the invention without knowing the identify of the physiological ligand.

The ligand preparation procedure, briefly illustrated in Section B of FIG. 1, used by the present invention is based on Phage Display of Peptides and Proteins: A Laboratory Manual (1996) Acad. Press N.Y. eds. Kay, B., Winter, J., and McCafferty; J.; Cwirla, S. E., et al. (1990) PNAS USA, 87:6378–6382; and Barrett, R. W. et al. (1992) Anal. Biochem. 204:357–364, all of which are incorporated herein by reference. In this procedure, biotinylation of target proteins, phage panning, phage purification, estimation of peptide-phage affinity for target protein, and preparation and purification of phage DNA for sequencing are performed in 96-well format.

In one embodiment of the invention, solution phase panning followed by capture of phage on microtiter plates is used. For solution phase panning, the target proteins obtained and purified as described above and illustrated in Section A of FIG. 1 are biotinylated using sulfo-NHS-LC-LC-biotin according to the procedure recommended by the manufacturer (Pierce, Rockford, Ill.). Free biotin may be removed by passing through a gel filtration using D-Salt polyacrylamide 6000 columns (Pierce Chemical Co.). The extent of biotinylation of target proteins may be estimated by the [2-(4'-hycroxyazobenzene) benzoic acid] (HABA) method (Green, N. M. (1965) Biochem. J., 94, 23c–24c), or proteins may be used without measurement of biotinylation. Using sulfo-NHS-LC-LC-biotin according to the procedure recommended by Pierce (Rockford, Ill.), target proteins are routinely biotinylated to the extent of 1–10 biotin molecules per target protein. Multiple proteins may be biotinylated in polypropylene microtiter dishes and separated from free biotin by passing through Sephadex G-50 (Pharmacia Biotech) packed into 96-well Multiscreen Minicolumns (Millipore Corporation).

Referring again to FIG. 1, Section B, biotinylated target proteins (0.05 ug–1.0 ug) in 90 ul 50 mM Tris-HCL, 150 mM HaCl, pH 7.5, containing 0.5% Tween-20 (wash buffer A) are added to phage ($10^{11}$ pfu) from a peptide phage library such as those available from New England Biolabs, Beverly, Mass. (for example, Ph.D.-12, Ph.D.-7, or Ph.D.-cyc7) in a 96-well polypropylene microtiter plate (one protein per well) and incubated for 1 hour at room temperature. The phage library can be prepanned against streptavidin to eliminate the phages that are specific for this protein. Each solution corresponding to each protein is then transferred to a well of a 96-well streptavidin coated plate (one solution per well). These streptavidin coated plates are either obtained from Pierce, or prepared by incubating Nunc Maxisorp plates overnight at 4 C. with 15 ug streptavidin in 150 ul of 0.1M NaHCO3 pH 8.6, followed by incubation with blocking). Prepared Nunc Maxisorp plates are capable of binding 0.025 ug of biotinylated target protein as measured by binding of horseradish peroxidase-labeled biotin (Pierce Chemical Co.). After a 20 minute incubation, biotin is added to each well solution to a final concentration of 0.1 mM and incubation continued for 5 minutes. The plate is washed with several volumes of wash buffer A and phage bound to the protein target are eluted by adding 100 ul of 0.2 M glycine HCl, pH 2.2, to each well and incubating for ten minutes. The acid solution containing the released phage is removed from each well and transferred to a well of a 96 well polypropylene microtiter plate containing 15 ul of 1 M Tris-HCl, pH 9.1.

Alternatively, panning is carried out essentially following the protocol of New England Biolabs recommended for Phage Display Peptide Library Kit. Target proteins (5 ug in 150 ul 0.1M NaHCO3, pH 8.6) are added to each well of a 96 well microtiter plate (Costar 9017 or Nunc Maxisorp) and incubated at 4 C. overnight with gentle shaking. The protein solution is then removed, and wells are filled with blocking buffer (0.1 M NaHCO3, 5 mg/ml BSA, pH 8.6). The plate is incubated three hours at 4 C. then the blocking buffer is removed and the plate washed with wash buffer A. Next, $10^{11}$ plaque forming units (pfu) from a peptide phage library are suspended in wash buffer A and incubated for one hour at room temperature. The microtiter plate is washed with wash buffer A. To elute the phage, 100 ul of 0.2 M glycine HCl, pH 2.2, is added to each well and incubated ten minutes. The acid solution is removed from each well and added to the wells of a 96 well polypropylene microtiter plate containing 15 ul of 1 M Tris-HCl, pH 9.1.

From each of the 96 wells, the eluted phage (now in a total volume of 100 ul) is amplified in 2 ml of LB media containing 1:100 dilution of overnight culture of *E. coli* strain ER2738 (New England Biolabs) (or other *E. coli* strain containing the F-factor). This amplification is performed in eight sterile 12-well plates, using Qiagen Air Pore strips (Qiagen, Valencia, Calif.) to prevent spillage. After 4.5 hours, the samples are transferred to a 96-well deep well plate (one sample per well) and centrifuged at 3,000×g to pellet the *E. coli* cells. The 96 supernatants containing the phage are transferred to a 96 deep well plate (one supernatant per well) and a ⅙ volume of PEG/NaCl (20% w/v polyethylene glycol 8000, 2.5 M NaCl) is added. The solution is incubated at 4° C. overnight. After overnight precipitation at 4° C., samples are spun for 30 minutes at 5600×g in a Qiagen 4–15° C. centrifuge to pellet the phage. Each of the 96 supernatants is removed and the phage are resuspended in 100 ul wash buffer A. Phage yields of $10^{10}$–$10^{11}$ pfu are routinely obtained by propagation of eluted phage in 2 ml of cell culture, which provides an adequate number of phage for subsequent rounds of panning. Alternatively, *E. coli* cells can be removed and the supernatant containing the phage collected by filtration instead of centrifugation as is known in the art.

Amplified phage is used in second and third rounds of panning and 100 ul of each amplified phage (typically $10^{10}$ to $10^{11}$ pfu) are added to its corresponding target protein as described above. Panning is carried out in identical manner except that wash buffer may contain concentrations of Tween-20 up to 0.5% (v/v). Phage may be titered as described below or the entire 100 ul of amplified phage may be used for panning without estimation of phage titer. After the third round of affinity panning, phage may be titered.

The titer of a phage stock may be estimated after each of the amplification steps, or the titer of phage eluted after panning may be estimated. To estimate phage titer, phage may be serially diluted in polypropylene microtiter plates and spotted onto a cell lawn. Wells of a microtiter plate are filled with 90 ul TBS (50 mM Tris HCl, pH 7.5, 0.15 M NaCl). Ten microliters of phage are transferred by multichannel pipettor to the first row of the plate, mixed by pipetting up and down multiple times. From this row 10 ul is transferred to the next row until the last row is reached. Phages are thus diluted over a $10^8$-fold range. In this method, the 96 phage samples may be diluted for titering using 8 microtiter plates. Using a multichannel pipettor, 2 ul of solution are removed from a column of wells in the microtiter plate and spotted onto LB agar plates that contain IPTG (200 uM) and Xgal (190 uM) and that are overlaid with top agar mixed with a saturated culture of *E. coli* ER2738 (New England Biolabs), or other *E. coli* strain containing F-factor. Sixteen such agar plates are necessary to estimate the titer of the 96 phage samples. Agar plates are incubated approximately 16 hours at 37° C. and phage are visualized as blue plaques to estimate titer of the phage stock. Phage titer is calculated by observing the greatest phage dilution that produced individual phage plaques on the agar plate.

Following three rounds of affinity panning, individual plaques are isolated by pipetting an appropriate dilution, based on the phage titer described above, of eluted phage from the third round of affinity panning onto LB/IPTG/X-gal agar plates described above. One agar plate is needed for each eluted phage sample (i.e. 96 agar plates are required to obtain individual phage from panning against 96 targets). Plates are incubated overnight at 37° C. to produce blue plaques. As many as twelve individual plaques from each plate are transferred separately into 500 ul of a 1:100 saturated culture of *E. coli* ER2738 diluted in LB in 96-deep well plates and amplified at 37° C. with vigorous shaking for 4.5 hours. Twelve 96-well deep plates are needed for the 96 targets. Phage may be separated from cells using a Uniplate filter plate as described above. Phage in the cell-free media may be titered as described above and used for a phage ELISA.

To determine which individual phage binds most tightly to a target protein, a phage ELISA is used. The ELISA is carried out essentially the same as the NEB protocol except 3,3',5,5'-tetramethylbenzidine (TMB) (KPL, Gaithersburg, Md.) is used as the horseradish peroxidase (HRP) substrate. ELISA signals are read at 600 nm in a mitrotiter plate reader such as Spectrafluor (Tecan). Individual phage are diluted so that all phage samples are at equal concentration (typically $2 \times 10^8$ to $2 \times 10^9$ pfu in 50 ul of wash buffer A). The individual phage are transferred to wells coated with the target protein as described in the direct panning method described above. In the case of solution phase panning, biotinylated target proteins are added to streptavidin plates and then phage are added to microtiter plate. Phage are allowed to bind as described in panning steps above except that after washing unbound phage from the plate, 150 ul of a 1:5000 dilution of HRP-labeled anti-M13 antibody (Pharmacia Biotech, Piscataway, N.J.) is added to each well and incubated, then removed and the wells are washed. The HRP substrate TMB (KPL, Gaithersburg, Md.) is added and absorbance at 600 nm is monitored. Preferably, only those phage which show the highest affinity, are used in the method and kit of the present invention. Individual phages with the highest affinity for their corresponding target protein are sequenced by propagating the phage in 96-well deep well plates, whereby phage DNA is prepared in the 96-well format using an existing kit (Qiaprep 96 M13 kit; Qiagen, Valencia, Calif.) according to the manufacturer's recommended procedure. In the case of NEB phage libraries, phage DNA is sequenced using the primer supplied with the Ph.D. Phage Display Kits.

Table I

Table I shows examples of surrogate ligand sequences obtained by following the panning protocol described above.

The library used is HyB, obtained from Display Systems Biotech, Vista. Calif. Phage ELISA performed using direct coating of microtiter wells with 5 ug target protein and $10^9$ pfu of individual phage results in ELISA signals above background wells (containing no target protein) for the two target proteins.

| Phage ID | Sequence |
|---|---|
| Target Protein #1: Arabidopsis GDP-mannose-pyrophosphorylase | |
| 1h12 | S G R V R P A G |
| 1e12 | G R K L E R N R |
| 1f3 | G R K L E R N R |
| 1f12 | I R R K T E G T |
| 1a3 | G G G T F G G A |
| Target Protein #2: Bacillus thuringensis vip2 | |
| 1f8 | A G R F K A F R |
| 2b5 | M G P G G R L G |
| 2g5 | A A R S G R S D |
| 2a5 | A E G L R G W G |
| 1a8 | E R A I W D R D |
| 1b8 | S V R R E T M D |

These two examples of Table 1 show how surrogate ligands cluster around a consensus sequence (G R K L E for target protein #1, A X G G/L R D for target protein #2). They also show how outsiders that have no physiological significance are identified by their lack of consensus sequence (phage ID 1a3 in target #1).

Using the method of the present invention, sets of surrogate ligands are obtained, where each surrogate ligand in each set of surrogate ligands binds selectively to one of the desired target proteins. Thus, a set of surrogate ligands is generated for each desired target protein. In one embodiment of the present invention, the surrogate ligands bind selectively to a plurality of target proteins of unknown function.

A surrogate ligand "binds selectively" when it binds to its target in such a way that the binding can be readily distinguished from its binding to other targets because a) the signal generated is higher than the background signal and b) the binding is of much higher affinity for the specific target than it is for non-specific ones (the signal obtained from binding to non-specific targets is weaker or non-existent).

As an alternative to phage libraries displaying multiple copies of a peptide on a single phage, monovalent phage that display one or less peptides/phage may be used by the method of the present invention. Using monovalent phage may result in higher affinity phage. Lowman, H. B. (1997) Annu. Rev. Biophys. Biomol. Struct. 26:401–24 One such phage library, HyB, can be obtained from Display Systems Biotech, Vista. Calif. Using the HyB library, phage can be panned and propagated as described above except that helper phage M13KO7 must be added during phage amplification for production of phages. In this phagemid system, the displayed peptide is linked to the human secretory trypsin inhibitor, (PSTI) which is in turn displayed on the g3 protein of the filamentous phage. Rottgen, P., and Collins, J. (1995) Gene 164:243–250. Such a system may result in peptide phage of higher affinity than polyvalent display. Green, N. M. (1965) Biochem. J., 94:23c–24c Also in this system, the PSTI protein displaying the selected peptide may be transferred to an expression vector and purified in illigram quantities from one liter cell culture. Maywald, F. et al. (1988) Gene 68:357–369)

In another embodiment of the present invention, the peptidic surrogate ligand can be replaced by a RNA aptamer. The method for selection and preparation of such RNA aptamers has been published (for review see: Famulok, M (1999) Curr. Opin. Struct. Biol. 9:324; Herman, T and Patel, D. J. Science (2000), 287:820–825); Kelly, J A, Feigon, J, Yeates, (1996) J. Mol. Biol. 256:417; and Feigon, J, Dieckmann, T and Smith, F. W. (1996) Chem. Biol. 3: 611). The peptidic surrogate ligand can also be replaced by a beta-peptide. Beta-peptides are composed of beta-amino acids, which contain an additional methylene group in the peptidic backbone (Seebach, D and Matthews, J. L. (1997) Chem. Comm. 2015–2022; Gellman, S (1998) Acc. Chem. Res. 31:173–180). Because of the expected increased stability of beta-peptide versus natural peptides, the surrogate ligands thus generated are expected to be shorter than natural peptide surrogate ligands and therefore might simplify the complexity of the pool of surrogate ligands that need to be screened to identify a ligand for each of the target proteins. The selection of the appropriate beta-peptide surrogate ligand for each target protein can be based on protocols used for some collections of natural peptides such as Yaffe et al. (1997) Cell, 91:961–971. These protocols select the specific ligand by presenting the collection of ligands to the protein target and subsequent separation of the complex by gel filtration. The selected ligand is then identified by mass-spectrometry.

High Throughput Multiplexed Displacement Assay

The multiplexed HTS displacement assay of the present invention incorporates the technology developed by Luminex Corporation, Austin Tex. This technology provides a collection of one hundred 5 um microspheres ("beads" or "particles") individually labeled by a defined combination of two dyes. The surfaces of the beads are modified to allow coupling of an analyte (nucleic acid, protein, or other such material) to the beads. The analyte is also labeled, preferably with a fluorescent molecule (nucleic acid, protein, or other such material). The bead identity, and therefore the identity of the analyte coupled to it, is determined by flow cytometry. Since one hundred different beads are available, the interaction of one hundred different analytes with their corresponding fluorescent label can be measured at the same time. The Luminex multiplex assay is described in U.S. Pat. No. 5,981,180, which is incorporated herein by reference. While current Luminex beads carry two dyes, allowing the encoding of one hundred beads, three dyes are possible and would allow the simultaneous encoding of one thousand beads and corresponding target proteins.

Once the surrogate ligands are identified and sequenced by the method of the present invention as described above, they may be synthesized by and obtained from a commercial supplier of peptides. In the preferred embodiment of the present invention, the surrogate ligands have a N or C terminal cysteine residue. For cost saving reasons, it is preferred to have the cysteine as C-terminal rather than N-terminal. The Merrifield peptide synthesis procedure starts at the C-terminal and a large amount of Cys-resin can be prepared and used for all the peptide synthesis work. An amount of 1 mg of peptide is sufficient for use by the method of the present invention.

According to the method of the present invention, each surrogate ligand of the present invention is coupled to individually labeled and detectable Luminex beads to form what is referred to herein as a ligand-bead complex. The term "complex" refers to the structure formed upon connection of ligand to bead. Target proteins bind selectively to their respective ligand-bead complexes to form sets of target modules of the invention. For example, a particular target protein binds selectively with a particular ligand-bead complex to form a first target module. Another target protein binds selectively with another (or the same) ligand-bead complex to form a second target module, and so on.

One embodiment of the method of the present invention uses avidin-linked phycoerythrin to label the target proteins. The symbols $\lambda_{ex1}$, $\lambda_{em1}$ indicate the excitation and emission wavelengths for bead identification. The symbols $\lambda_{ex2}$, $\lambda_{em2}$ indicate the wavelengths for measuring the fluorescence associated with the bead. Alternatively, the target proteins can be labeled with a fluorescent group compatible with the Luminex technology. An example of such group is the Alexa 532 dye (Molecular Probes, Eugene, Oreg.) or Cy5 (Pharmacia).

The assay of the present invention is performed by incubating the sets of target modules in each well of a microtiter plate (either 96 or 384-well format). The reaction volume can be between 10 and 100 ul. The buffer used can be adapted to each instance but is typically PBS or 100 mM Tris-HCl at pH 7.5 with 0.1 M NaCl. In one embodiment, 1000 to 5000 beads comprise each set of specific target modules and are present, with 0.1 to 100 nM of a target protein and 0.1 to 100 nM of avidin-phycoerythrin, in each well of a microtiter plate. In addition, the well contains 1 to 10 uM of test compound in a final concentration of DMSO of 1 to 5%. Thus, in one embodiment, 100,000 to 500,000 beads (representing the sets of target modules) are present in the same final volume of 10 to 100 ul. The reaction mixtures are incubated at room temperature for 1 to 30 minutes and analyzed using a Luminex detection apparatus.

Figure 2A:
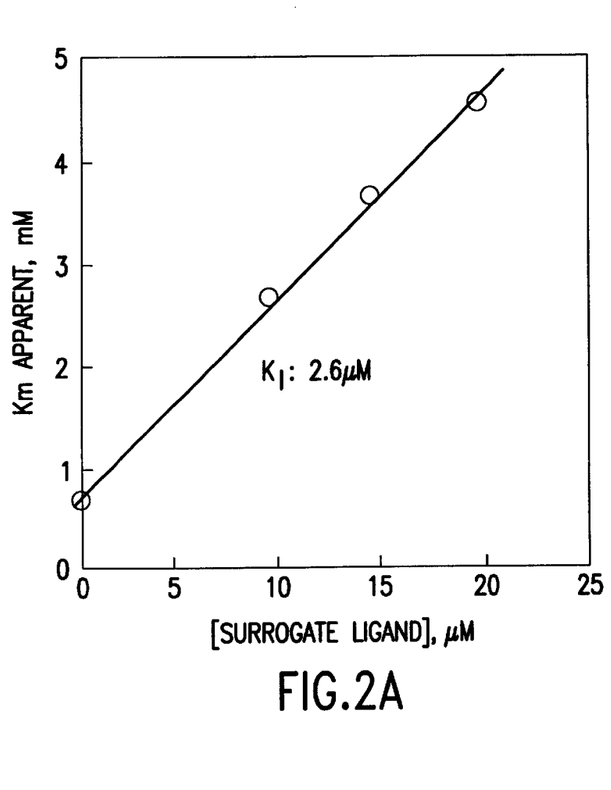
FIG. 2A is a graph which shows the inhibition constants of a surrogate ligand identified for a target protein as measured by enzyme inhibition.
Figure 2B:
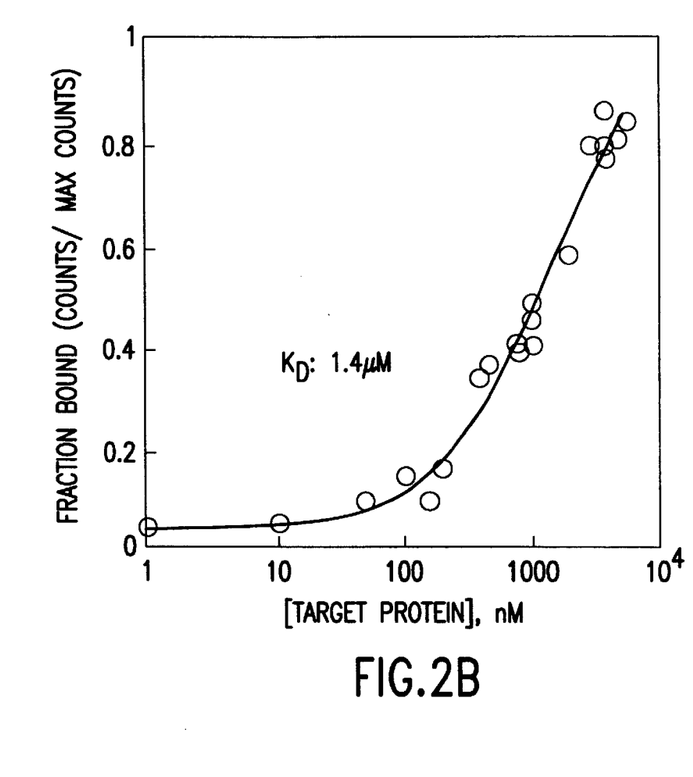
FIG. 2B is a graph which shows the affinity constant for the same surrogate ligand and same protein illustrated in FIG. 2A as measured in a Luminex™ bead set-up in which the ligand is bound to the bead.

The present invention recognizes that the physical entity analyzed and measured by the present invention is the selective binding of the target protein to its corresponding surrogate ligand. Steps were taken to ensure that this physical entity was biochemically meaningful. As an example, the inhibition potency of a surrogate ligand, as defined by its $K_I$ and measured by an enzymatic assay was compared to its affinity for the target protein, as defined as its $K_D$ and measured in a Luminex bead assay set-up. This comparison, shown in FIGS. 2A and 2B, demonstrates that the two values are essentially identical.

The present invention also recognizes that the target proteins will often present more than one relevant binding site, for example, kinases have a catalytic site which binds the substrate and ATP and a protein interaction site that interacts with the protein directly upstream in the signal transduction pathway. Surrogate ligands are identified for each of these sites. By binding each of these surrogate ligands to a different bead, the different sites are probed simultaneously.

For some applications, the present invention also recognizes that it is advantageous to have the target protein rather than the surrogate ligand bound to the bead. In this case, the target protein is linked to the bead by covalent bound formation with the reactive groups present on the bead surface or by interaction with avidin coated beads. The surrogate ligand is free in solution and labeled either with biotin, for detection via avidin-phycoerythrin, or with a fluorescent dye such as Alexa 532 or Cy3 for direct detection.

The present invention also recognizes that the Luminex technology can be replaced with technologies that also identify beads with a specific marker. For example, one such marker system is referred to as the Quantum Dot™ (Quantum Dot Corporation, Palo Alto, Calif.). The Quantum Dot™ is a 2–10 nm CdSe crystal which, depending on its size, emits a single wavelength light ranging from ultraviolet to infrared when excited with UV light (Chan and Nie (1998), Science 281:p2016–2018). In this approach, each bead, either a polymer bead or a glass bead, is identified by a defined popluation of quantum dots. The complexity of the quantum dot population defines the total number of distinct beads that can be encoded. The complexity of a set-up defined by the presence of absence of a given quantum dot is calculated by: complexity=$2^{(number\ of\ different\ quantum\ dots)}-1$. For example, if five quantum dots are used, 31 beads can be encoded. The complexity of a set-up defined by the absence, low amount or high amount of a given quantum dot is given by: complexity=$3^{(number\ of\ different\ quantum\ dots)}-1$. For example, if five quantum dots are used, 242 beads can be encoded. It can be seen that, even with a small number of quantum dots, a larger collection of beads can be encoded. This allows the use of quantum dots with well separated emission, which in turn allows the detection and identification of the bead to be performed by a low cost imaging system. Such a system can be a microscope with a UV light source, a mechanical stage holding a 96-well plate controlled by a computer and a color digital camera such as the ones used for computer work. The reaction in each well is composed of the same elements as for the Luminex approach but with the quantum dot encoding beads replacing the Luminex bead. After allowing the beads to settle at the bottom of the well, the 96-well plate is scanned on the microscope, the image captured and analyzed by computer. This setup needs only to discriminate between the five quantum dot colors and a six color for the fluorescence associated with the bead due to the bound fluorescent ligand. This last source of fluorescence can also be a six quantum dot of a color different from the bead encoding.

Alternatively, a microfluidics set-up such as the one available from Caliper Technologies (Caliper, Mountain View, Calif.) can be used by the present invention. In this case, both the surrogate ligand and the target protein are free in solution. The surrogate ligand is labeled with a fluorescent such as fluorescein, tetramethylrhodamine or other. The detection of the interaction is done by fluorescence polarization as is known in the art. Fluorescence polarization methods suffer from a lack of sensitivity and the need for a large amount of target protein. A typical concentration of such protein is 10 to 50 uM. In the case of a 50 kDa protein assayed in a 25 ul assay volume, 1.25 to 6.25 grams of protein are needed to assay 100,000 compounds. These large amounts are incompatible with a Genomics based HTS. By using a microfluidics set-up, the reaction volume is reduced to 10 nl or less, requiring 500 ug or less of the target protein. In this case, each compound is sampled against each target in a serial fashion.

The present invention also includes a screening kit comprising a set of target modules representing the whole complement of expressed proteins in a given organism, or for a subset thereof such as the proteins involved in a specific metabolic or signaling pathway. The ligand-bead complexes are stably stored in a sterile fashion at 4° C. The corresponding plurality of protein targets are stored as aliquots in a sterile fashion at −80 C. Alternatively, the sets of target modules are constructed and stored in the individual chambers of a multi-chamber container. The kit of the invention is used, in part, to associate potentially useful protein targets with test compounds.

One advantage of the present invention is that it provides for a huge increase in datapoints collected per day compared to traditional HTS of target proteins. Since the method and kit of the invention are formatted for 96 or 384 well plates, the process is adapted to a robotic platform consisting, for example, of a TomTec Quadra 96plus (TomTec, Hamden, Conn.) for assembling the reactions and a Hudson Plate-Crane (Hudson Control Systems) to deliver the assembled plates to a Luminex/HTS detection apparatus. Thus, the method and kit of the present invention analyzes one 384-well plate every 20 minutes. When one-hundred targets are multiplexed and a single small molecule is present per well, the output of the present invention is 115,200 datapoints per hour. When 24 plates are assayed in a daily cycle of 10 hours, the method and kit of the present invention collects 1.1 million datapoints per day. As a comparison, a survey of forty-three Life Science companies involved in HTS showed that the estimated datapoint collection is between 135,000 to 175,000 each month for 1999 and expected to grow to 490,000 to 615,000 monthly in the year 2002 (High Throughput Screening: 1999–2000 Market analysis for Life Science Manufacturers, Clinical Marketing Consultants, Boulder, Colo.). In the same survey, these companies do not expect a decrease in price per datapoint, making the collection of data on a genome size collection of targets out of reach economically.

Furthermore, the method of the present invention makes a very efficient use of the compounds to be screened: only a very small amount of each compound is consumed to test a large number of targets. As an example of the present method and kit, a 100 ul assay volume containing 100 targets and a compound collection with an average MW of 500 tested at 2 uM, a 100 target test would require 100 ng of compound (or 1 ng per target). Based on the survey mentioned above, a typical assay uses a 384-well format using 50 ul volume per well. Since only one target is assayed per well, the equivalent amount of compound that would be needed to run 100 targets, in the traditional HTS format, is 5 ug (or 50 ng per target).

Another advantage of the present invention, is that it provides a HTS method and kit that screens for proteins of unknown function.

The above-disclosed embodiments are illustrative. This disclosure of the invention will place one skilled in the art in possession of many variations of the invention. All such obvious and foreseeable variations are intended to be encompassed by the appended claims.

What is claimed is:

1. A method comprising:
   a) obtaining a plurality of target proteins;
   b) obtaining a first set of surrogate ligands, wherein each surrogate ligand in said set of surrogate ligands is a peptide and binds selectively to a first target protein;
   c) binding said first set of surrogate ligands to first detectable beads to form a first set of surrogate ligand-bead complexes, wherein said first detectable beads can all be detected by the optical characteristics of said first detectable beads;
   d) combining said first set of surrogate ligand-bead complexes with said first target protein labeled for detection to form a first target module;
   e) repeating steps a, b, c and d, either concurrently or subsequently with a different set of surrogate ligands and detectable beads, and with either said first target protein or a different target protein, to form sets of target modules;
   f) adding said sets of target modules to each chamber of a multi-chamber container;
   g) adding a test compound, or a collection of test compounds, to each chamber of said multi-chamber container;
   h) detecting displacement of a target protein with a test compound; and
   i) determining the identity of each target protein that is displaced with a test compound.

2. The method according to claim 1, wherein obtaining each said set of surrogate ligands comprises:
   a) obtaining a phage library, wherein each phage of said library displays foreign peptides;
   b) mixing said phage library with each said target protein of said plurality of target proteins;
   c) isolating phages displaying said foreign peptides that bind selectively to each said target protein;
   d) isolating DNA encoding said foreign peptides that bind to each said target protein;
   e) sequencing said DNA; and
   f) synthesizing said set of surrogate ligands based on said sequencing.

3. The method according to claim 1, wherein said set of target proteins are obtained by:
   a) selecting target genes from a genome;
   b) expressing each of said target genes to produce said set of target proteins; and
   c) purifying said target proteins.

4. The method according to claim 1, wherein the target protein in step (e) is said first target protein.

5. The method according to claim 1, wherein the target protein in step (e) is a target protein different from said first target protein.

6. The method according to claim 1, comprising:
   a) biotinylating said target proteins; and
   b) linking said target proteins with avidin-phycoerythrin.

7. A method according to claim 1, wherein said surrogate ligand is a peptide.

8. A method according to claim 1, wherein said surrogate ligand is a RNA aptamer.

9. A method according to claim 1, wherein said surrogate ligand is a beta-peptide.

10. A method according to claim 1, comprising labeling each said individual bead with a defined combination of two dyes.

11. A method according to claim 1, comprising labeling each said individual bead with a defined combination of three dyes.

12. A method according to claim 1, comprising labeling each said individual bead with a defined population of quantum dots.

13. A method according to claim 10, wherein the number of said sets of target modules is 100 such that 100 target proteins are screened in each said chamber.

14. A method according to claim 1, wherein the amount of said compound used per said chamber falls within the range of 0.1 to 100 ng.

15. A method according to claim 1, wherein the enzymatic or regulatory function of each said target proteins of said plurality of target proteins is unknown.

16. A kit for screening a plurality of target proteins from a genome comprising:
   a) sets of target modules, wherein each set of said sets of target modules comprises:

(1) individually detectable beads;
(2) a set of surrogate ligands attached to said detectable beads, wherein the surrogate ligands of said set of surrogate ligands are peptides and are bound selectively to the same or different target protein of said plurality of target proteins;
(3) wherein said target proteins are labeled for detection; and b) a multi-chamber container, wherein said sets of target modules are stored in each chamber of said mult-chamber container.

17. A kit according to claim 16 wherein said plurality of target proteins are of unknown function.

18. A kit according to claim 16 wherein the number of said target proteins is greater than 50.

19. A kit according to claim 16 wherein the number of said target proteins is greater than 500.

20. A kit for screening a plurality of target proteins from a genome comprising:
    a) a set of ligand-bead complexes, wherein each said ligand-bead complex comprises:
       (1) a detectable bead;
       (2) a surrogate ligand comprising a peptide attached to said detectable bead;
    b) a plurality of target proteins, each said target protein of said plurality of target proteins is capable of selectively binding to a surrogate ligand; and
    c) a multi-chamber container, wherein said plurality of ligand-bead complexes are stored in each chamber of said multi-chamber container, said target proteins being stored separately from said ligand-bead complexes.

21. A kit according to claim 20 wherein said target proteins are of unknown function.

22. A kit according to claim 20 wherein the number of said target proteins is greater than 50.

23. A kit according to claim 20 wherein the number of said target proteins is greater than 500.

24. In a method for high throughput screening using individually detectable beads, surrogate ligands, and a plurality of target proteins, the improvement comprising,
    a) combining in each chamber of a multi-chamber container sets of target modules,
       i) wherein each target module within each set of said sets of target modules comprises a ligand-bead complex and a target protein labeled for detection;
       ii) wherein said ligand-bead complex comprises a surrogate ligand comprising a peptide coupled to an individually detectable bead;
       iii) wherein each said surrogate ligand binds selectively to one of said target proteins;
    b) adding to each said chamber of said multi-chamber container a test compound, whereby said compound displaces said target proteins from said target modules to which said target compounds interact;
    c) detecting displacement of a target protein with a test compound; and
    d) determining the identity of each target protein that is displaced with a test compound.

25. The method according to claim 24, wherein the function of said plurality of target proteins are unknown.

26. The method according to claim 24, wherein obtaining each said set of surrogate ligands comprises:
    a) obtaining a phage library, wherein each phage of said library displays foreign peptides;
    b) mixing said phage library with each said target protein of said plurality of target proteins;
    c) isolating phages displaying said foreign peptides that bind selectively to each said target protein;
    d) isolating DNA encoding said foreign peptides that bind to each said target protein;
    e) sequencing said DNA; and
    f) synthesizing said set of surrogate ligands based on said sequencing.

27. The method according to claim 24, wherein said set of target proteins are obtained by:
    a) selecting target genes from a genome;
    b) expressing each of said target genes to produce said set of target proteins; and
    c) purifying said target proteins.

* * * * *